United States Patent [19]

Schneider

[11] 3,941,482

[45] Mar. 2, 1976

[54] METHOD OF TESTING ALKALI HALIDE CRYSTALS WITH ANISOTROPIC CENTERS

[75] Inventor: Irwin Schneider, Alexandria, Va.

[73] Assignee: The United States of America as represented by the Secretary of the Navy, Washington, D.C.

[22] Filed: Feb. 25, 1975

[21] Appl. No.: 552,906

[52] U.S. Cl................ 356/114; 350/160 R; 356/30
[51] Int. Cl.² ........................................ G01J 4/00
[58] Field of Search ............. 356/30, 114; 350/160; 340/173 CC

[56] References Cited
UNITED STATES PATENTS

| | | | |
|---|---|---|---|
| 3,466,616 | 9/1969 | Bron et al..................... | 340/173 CC |
| 3,720,926 | 3/1973 | Schneider..................... | 340/173 CC |

OTHER PUBLICATIONS

Compton & Rabin:, "F. Aggregate Centers in Alkali Halide Crystals," *Solid State Physics*, Vol. 16, Seitz & Turnbull Eds., Academic Press, N.Y., 1964.

*Primary Examiner*—John K. Corbin
*Assistant Examiner*—Richard A. Rosenberger
*Attorney, Agent, or Firm*—R. S. Sciascia; Arthur L. Branning; Thomas McDonnell

[57] ABSTRACT

A method for determining the capability and optimum operating parameters of alkali halide crystals with anisotropic centers as holographic recording media by assessing the dispersion and absorption of polarized light by the anisotropic centers through a measurement of the difference in refractive index and absorption for light of different polarizations, the former through utilization of an ellipsometric technique wherein light passes successively through a polarizer, test crystal, analyzer, and detector.

5 Claims, 6 Drawing Figures

+ : ALKAI ION
- : HALIDE ION
$e^-$ : ELECTRON

METHOD OF TESTING ALKALI HALIDE CRYSTALS WITH ANISOTROPIC CENTERS

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention generally relates to a testing technique and in particular to a testing technique involving alkali halide crystals with anisotropic centers for capability as holographic media and for determining their optimum operating conditions.

Alkali halide crystals with anisotropic centers have shown promise as holographic recording and storage media in U.S. Pat. Nos. 3,580,688, 3,673,578, 3,720,926, 3,727,194, 3,771,150, 3,814,601, and 3,846,764. The advantages of these crystals include an on-line read-write-erase storage capability, minimal fatigue, reasonable writing sensitivity, nondestructive read, and thermal stability. The response of holographic media in wavefront reconstruction is generally characterized by diffraction efficiency which is defined as the ratio of diffracted to incident light intensity. As the diffraction efficiency increases, the reconstructed holograms are brighter.

Diffraction of light by a crystal is produced through general grating array variations of either absorption or refractive index. Phase patterns are clearly preferred since they generally give rise to much larger diffraction efficiencies in wavefront reconstruction.

The characterization of absorption differences is easily determined through standard spectrophotometric procedures, particularly for anisotropic centers which give rise to distinct easily measurable absorption bands in the visible, near infrared, and near ultraviolet spectral regions. However, the contributions of anisotropic centers to the refractive index of a crystal has been extremely difficult to measure because of their relative small contribution to the overall refractive index. Thus, it becomes difficult to accurately predict the phase contribution of anisotropic centers to the diffraction efficiency and therefore to properly prepare the crystal and to select the optimum operating parameters for use as a holographic recording medium. Techniques to determine this contribution such as Faraday rotation are usually cumbersome requiring very low operating temperatures and high magnetic fields and have been useful primarily in special cases involving highly isotropic centers such as F-centers, but not for the class of centers which are anisotropic. This lack of a quick and simple technique to directly measure the contribution to the index of refraction by anisotropic centers and thus their dispersion may very well be the underlying reason for the oversight of the predominant effect these centers have on the crystal diffraction.

SUMMARY OF THE INVENTION

It is therefore an object of this invention to provide a method for measuring the changes in the refraction index or more specifically the birefringence produced by oriented anisotropic centers in alkali halide crystals.

Another object of this invention is to correlate this birefringence with the degree of anisotropic center alignment from its dichroic absorption as determined from standard absorption measurements using linearly polarized light.

And another object of this invention is to provide a method for determining the spectral dependence of the diffraction efficiency of a crystal containing grating arrays of oriented anisotropic centers in alkali halide crystals and more specifically the wavelength for which the diffraction efficiency is a maximum.

A further object of this invention is to provide a method for selecting alkali halide crystals with anisotropic centers so that they have maximum capability as holographic media, i.e., maximum diffraction efficiency.

A still further object of this invention is to provide a guide for modifying the method of preparing alkali halide crystals in order to obtain high diffraction efficiency in holographic wavefront reconstruction.

And a still further object of this invention is to provide a method for determining the optimum operating parameters for alkali halide crystals as holographic media.

These and other objects are achieved by measuring the induced birefringence of an alkali halide crystal accompanying the alignment of anisotropic centers using an ellipsometric method which comprises the steps of linearly polarizing light of a given wavelength polarized along an axis of the crystal; entering the linearly polarized light in the crystal perpendicular to the surface of the crystal; passing the light through the crystal whereupon the light in general becomes elliptically polarized due to the birefringence of the crystal lattice induced by the previously optically aligned anisotropic centers; passing the light successively through an analyzer and detector; measuring the intensity of the light by rotating the analyzer for polarization parallel and perpendicular to the aligned centers; rotating the analyzer to obtain the maximum and minimum intensity of the elliptically polarized light passing through the analyzer; measuring the angle between the minimum intensity and the perpendicular intensity; measuring the optical density for light polarized parallel and perpendicular to the alignment of the anisotropic centers.

DETAILED DESCRIPTION OF THE INVENTION

Figure 1:
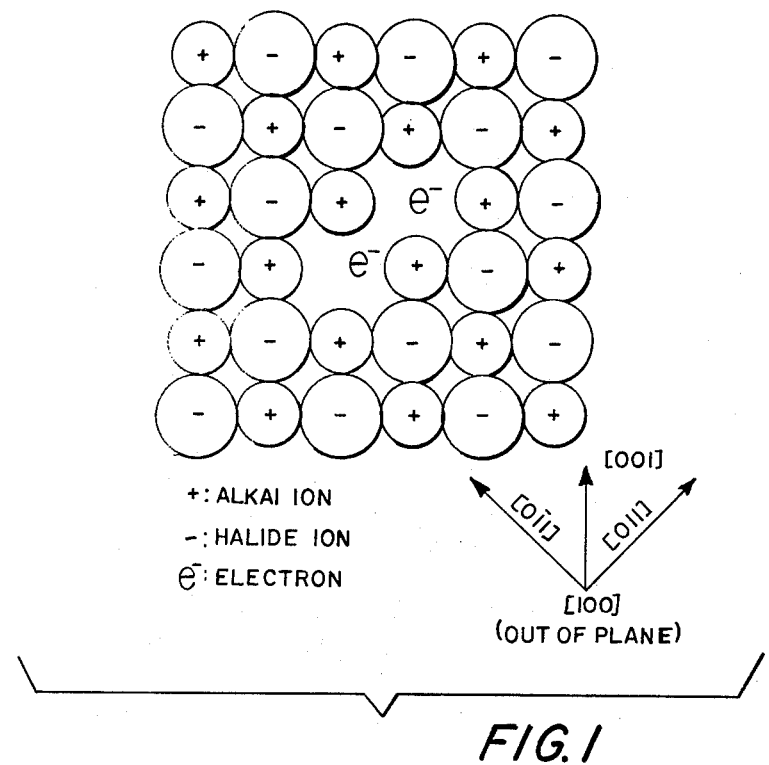
FIG. 1 is a schematic representation of one particular anisotropic color center, the M-center in an alkali halide crystal.

FIG. 1 shows a schematic section of an alkali halide crystal containing an M-center. An M-center consists of two F-centers, or two neighboring anion vacancies along a [110] axis each with one trapped electron. FIG. 1 shows a M-center with a vacancy axis specifically lying along the ⟨110⟩ direction. This center has three symmetry axes along which its optical dipole moments lie. One is the [011] vacancy axis which is the optical dipole direction for the M-band. The other two are [0$\bar{1}$1] and [100] perpendicular to this vacancy axis. These are usually associated with M-center transitions lying at energies greater than the M-band in the F-band spectral region.

It is through absorption of light in the F-band spectral region that M-centers are reoriented and can be aligned when linearly polarized light is used. For example, light which is linearly polarized along [0$\bar{1}$1] and is propagating along [100] would align all M-centers along the [0$\bar{1}$1] direction. An important consequence of the alignment is that M-center transitions can often be distinguished from overlapping absorptions of all isotropic and other unaligned anisotropic defects by simply subtracting the absorption measured with light of [0$\bar{1}$1] and [011] polarization.

It now has been discovered that the dispersion of light by M-centers and other anisotropic centers can be determined in a similar manner by aligning the anisotropic centers and by measuring the variation in the differences in refractive index for light polarized parallel and perpendicular to the alignment through a simple ellipsometric technique. As in most birefringent elements these two directions are analogous to the directions which are often referred to as the fast and slow directions. The subtraction which results through the method of this invention eliminates not only contributions due to other centers, but most important, dispersion due to the host lattice. It has further been discovered that although the contribution of anisotropic centers to the total refractive index is small, the contribution does lead to substantial phase variations and thus would result in high diffraction efficiencies in holographic storage.

Figure 2:
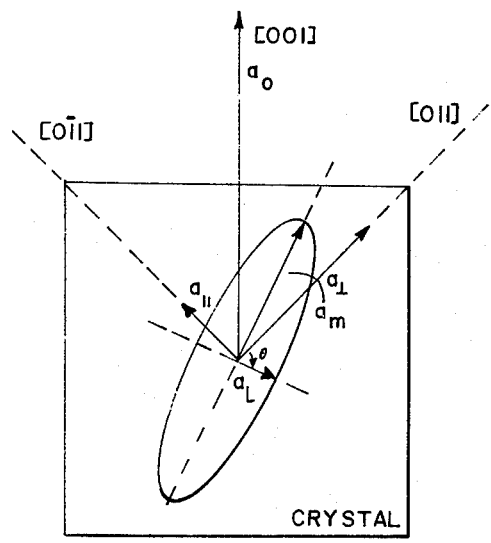
FIG. 2 is a schematic arrangement of an analysis of light elliptically polarized by aligned M-centers.

In order to better disclose the present invention reference is now made to FIG. 2. Light of an amplitude $a_o$ entering the crystal is linearly polarized along [001]. It is selectively absorbed by the M-centers and emerges ellipically polarized with amplitudes $a_{11}$ and $a_\perp$ as measured by an analyzer and detector oriented along [0$\bar{1}$1] and [011]. The relation between intensity which is determined by the detector and amplitude is $I = a^2$. These amplitudes have a phase difference given by $\delta = (2\pi d/\lambda)[n_{11} - n_\perp]$ wherein $n_{11}$ and $n_\perp$ are the refractive indices for light polarized along [0$\bar{1}$1] and [011], respectively, $\lambda$ is the wavelength of light in free space, and $d$ is the crystal thickness.

The amplitudes of the semimajor and semiminor axes of the ellipse, i.e., $a_M$ and $a_L$, respectively, and the orientation of the ellipse are determined by rotation of the analyzer for maximum and minimum transmitted intensity. Since the intensity is proportional to the square of the amplitude, these are related by the expressions:

$$I_M = a_M^2 = (a_\perp \sin\theta)^2 + (a_{11}\cos\theta)^2 + \frac{2a_{11}a_\perp \sin\theta}{\cos\theta \cos\delta}$$

$$I_L = a_L^2 = (a_\perp \cos\theta)^2 + (a_{11}\sin\theta)^2 - \frac{2a_{11}a_\perp \sin\theta}{\cos\theta \cos\delta}$$

wherein $\theta$ is the angle between $a_\perp$ and $a_L$. The expression for $\delta$ (phase difference) becomes:

$$\cos\delta = \frac{1 + \left(\frac{a_{11}}{a_\perp}\tan\theta\right)^2 - \left[\tan^2\theta + \left(\frac{a_{11}}{a_\perp}\right)^2\right]\frac{I_L}{I_M}}{2\sqrt{\frac{I_{11}}{I_\perp}}\tan\theta \left[1 + \frac{I_L}{I_M}\right]}$$

and for the difference in the refractive indices becomes:

$$n_{11} - n_\perp = \frac{\lambda}{2\pi d}\cos^{-1}\frac{1+[(a_{11}/a_\perp)\tan\theta]^2 - [\tan^2\theta + (a_{11}/a_\perp)^2](a_L^2/a_M^2)}{2(a_{11}/a_\perp)(1+a_L^2/a_M^2)\tan\theta}$$

In H. Kogelnik, Bell System Tech. J. 48, 2902 (1969) an expression for the diffraction efficiency of a mixed grating was derived as the sum of a phase and absorptive component and is as follows:

$$\eta = \left[\sin^2\frac{\delta'}{4\cos\theta_o} + \sinh^2\frac{D_o}{4(0.8686)\cos\theta_o}\right] \exp\left(-\frac{D_o'}{0.8686\cos\theta_o}\right)$$

wherein $\theta_o$ is the Bragg angle, $D_o'$ is the total optical density, $D_o$ is the total dichroic optical density modulation, and $\delta'$ is the total phase modulation.

For purposes of this invention $\delta' = \delta$. At any given temperature and for any given crystal and anisotropic center the ratio of $\delta$ and $D_o$ would be a constant depending on $\lambda$. It is therefore possible to set $dn/dD_o = 0$ and derive optimum values for both dichroic optical density and diffraction efficiency.

For example, suppose a crystal contains a completely aligned population of anisotropic M-centers and no underlying absorptions in the M-band spectral region. For this case $D_o'$ would equal $D_o$. Defining the parameter K as $\delta'/D_o$, the expression for the diffraction efficiency becomes:

$$\eta = \left[\sin^2\frac{KD_o}{4\cos\theta_o} + \sinh^2\left(\frac{D_o}{4(0.8686)\cos\theta_o}\right)\right] \exp\left(\frac{-D_o}{0.8686\cos\theta_o}\right)$$

Neglecting the absorptive component ($\sinh^2$ term), the diffraction efficiency would then have a maximum of $$\eta_{max} = \sin^2[\tan^{-1}(0.4343K)] \exp\left[-\frac{4.605}{K}\tan^{-1}(0.4343)K\right]$$

for a value of $$D_o^{max} = \frac{4\cos\theta_o}{K}\tan^{-1}(0.4343K).$$

For an identical crystal with incomplete alignment, the corresponding expressions are:

$$\eta_{max} = \sin^2[\tan^{-1}(0.4343pK)] \exp\left[-\frac{4.605}{Kp}\tan^{-1}0.4343pK\right]$$

for a value of $$D_o^{max} = \frac{4\cos\theta_o}{K}\tan^{-1}(0.4343pK).$$

Figure 3:
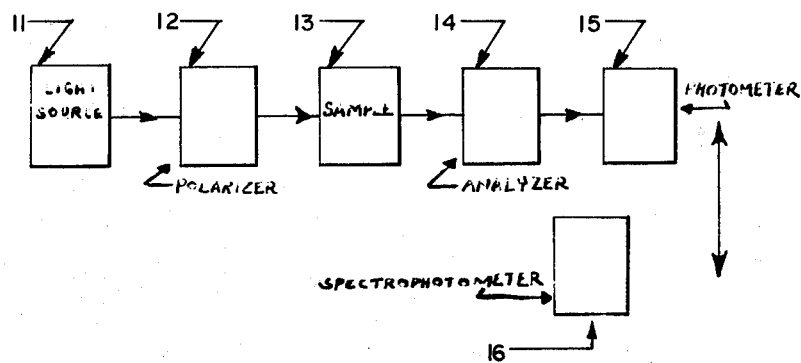
FIG. 3 is a schematic diagram of a means for analyzing a crystal anisotropic centers according to the practice of this invention.

From the above principles the method of this invention was developed. FIG. 3 shows a schematic diagram of means for carrying out the present invention. A light source 11 may be any apparatus capable of producing coherent or incoherent light at different selected wavelengths ranging over some select portion of the visible spectrum depending primarily on the anisotropic center of interest, and the host lattice used. The intensity of the light sources must be great enough to be detected after passing through all the elements shown in FIG. 3. Examples of suitable light sources would be either tunable dye lasers of the appropriate spectral output, e.g. for a NaF crystal the spectral output is from about 450 to about 600 mm, or an ordinary broad spectral region ranging source, e.g. tungsten, mercury, or xenon lamp.

The light passes through a linear polarizer, 12, which polarizes the light along a specific axis of the test specimen. Using aligned M-centers, the chosen incoming alignment direction would be [001] as depicted in FIG. 2. The invention places no limitation on the selection of the linear polarizer, although it is preferred that the polarizer have an extinction ratio of at least $10^5$:1.

The crystal, 13, which is being tested may be any alkali halide crystal with any aligned anisotropic centers preferably being tested at a temperature and spectral range for which the alignment has a nondestructive read. M-band excitation at room temperature in NaF is an example of one such preferred choice. Alternative anisotropic centers other than the M-center are the $M_A$ center which consists of an M-center adjacent to an anion impurity and the $F_A$ center which consists of an F-center adjacent to an anion impurity. The preferred alkali halides are NaF, KCl, and KF. The practice of this invention is not limited to any size or shape of the crystal.

The analyzer, 14, may be any device which like the polarizer, 12, can linearly polarize light and can be freely rotated for an accurate determination of the polarization angle. Again, it is preferred that analyzer, 14, be a high quality, commercially available linear polarizer with an extinction ratio of at least $10^5$:1.

The intensity of the light emerging from the crystal and analyzer is measured by a photometer, 15, and correlated with the optical density measured over the same spectral region using a spectrophotometer, 16, of standard design, e.g., the Cary 14MR spectrophotometer.

In the practice of this invention the crystal is set in place so that it has the proper orientation relative to the polarization of the incident light source, e.g., the [110] optical axis of the anisotropic M-center is set 45° with respect to the polarization of the incident light and the light source is adjusted to emit a light beam with a particular wavelength. The light enters and passes through the crystal perpendicular to its surface and becomes ellipically polarized. The light then enters an analyzer, 14 which can be rotated about an axis parallel to incidence for a maximum and minimum intensity determination thus yielding the amplitudes of the major and minor axes of the ellipically polarized light. The analyzer is then rotated so that its plane of polarization is either parallel or perpendicular to the alignment axis of anisotropic centers to determine both the angle $\theta$ between the minor axis and the direction perpendicular to alignment axis, and the amplitudes $a_{11}$ and $a_\perp$. These measurements are then repeated using other wavelengths until the spectral dispersion is measured for the entire spectral range of interest. Finally, the crystal is placed in the sample beam of a spectrophotometer, and the optical density is determined for light polarized parallel and perpendicular to the anisotropic centers, i.e., $D_{o11}$ and $D_{o\perp}$, respectively, can be determined.

From the collected data, $\eta_{max}$ is calculated at the various test wavelengths and is plotted against wavelength. Thus, the optimum performance capability for the particular alkali halide and anisotropic center as a holographic storage medium is quickly and easily determined as a function reconstruction read wavelength. The data also yields the spectral dependence of the performance capability of any particular crystal chosen.

The optical density is proportional to the product of the anisotropic center concentration and crystal thickness. From the aforementioned expressions for diffraction efficiency, the test results provide an accurate guide for selecting the exact amount of optical density needed to obtain a desired maximum diffraction efficiency. Thus the manufacturing process has the flexibility whereby either the crystal thickness be adjusted for a given color center concentration or the color center concentration be adjusted for a given crystal thickness so that the optimum optical density is achieved. By way of example the following experiment is given to demonstrate the utility of the present invention. It is to be understood the example is given by way of illustration and is not intended to limit the specification and the claims to follow.

EXAMPLE I

A 0.22 mm thick NaF crystal containing F-centers produced by coloring the crystal with 2-MeV electrons was exposed to unpolarized F-light to convert the F-centers to M-centers, and then to linearly polarized F-light for alignment of the M-centers along [0$\bar{1}$1]. See FIG. 1 for a schematic representation of the crystal. Measurements were carried out after producing randomly oriented M-centers and after successive exposures to [0$\bar{1}$1] F-light to produce increasing M-center alignment along [0$\bar{1}$1]. Absorption spectra measured were with light propagating along [100] and linearly polarized along [0$\bar{1}$1] and along [011]. The crystal was then placed in an ellipsometric arrangement wherein the phase angle $\delta$ was determined as a function of wavelength.

Figure 4A:
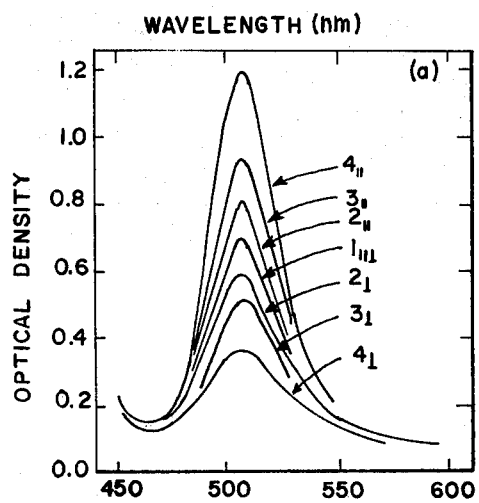
FIGS. 4A and 4B are absorption and dispersion spectra of M-centers in various stages of alignment illustrated for a particular NaF crystal (0.22 mm thick) colored with 2 MeV electrons and measured at room temperature.
Figure 4B:
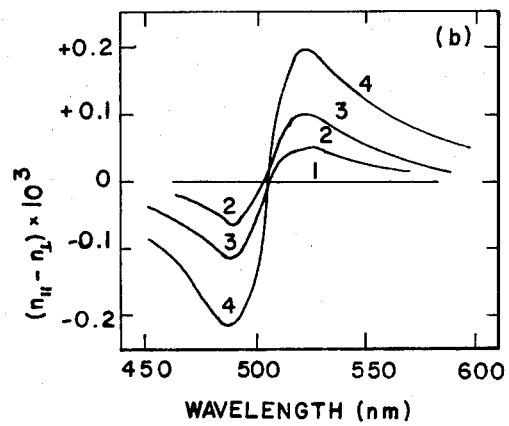
Figure 5:
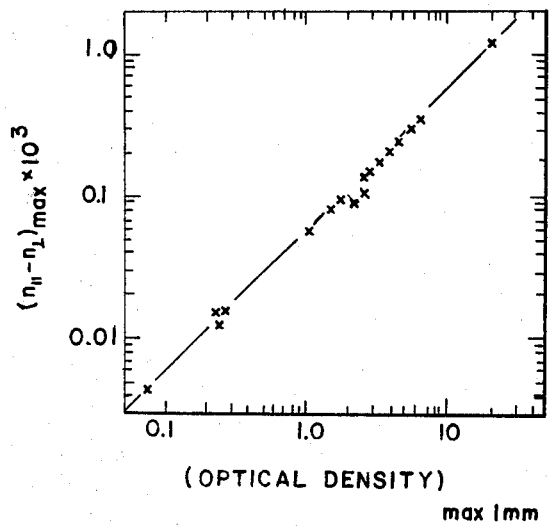
FIG. 5 is the variation of the maximum refractive index difference or birefringence with maximum optical density.

FIG. 4 shows that both the M-band dichroism, [0$\bar{1}$1]-[011] (see FIG. 4(a)), and the dispersion (see FIG. 4(b)) are initially zero for the case of randomly oriented M-centers (curves 1) but exhibit corresponding increases of dichroism and birefringence with each stage of M-center alignment (curves 2–4). As is typical for an anomalous dispersion curve of a single isolated transition, $n_{11}-n_\perp$ vanishes near the peak of the M-band and has maximum values of opposite sign on either side of it. FIG. 5 shows that the maximum index change, $(n_{11}-n_\perp)_{max}$, varies linearly with $D_o$/mm ($D_o$ is now the maximum peak-to-peak dichroic optical density) over a wide M-center concentration range with an average slope of $(0.055 \pm 0.001) \times 10^{-3}$. This linearity indicates that M-centers behave with regard to dispersion as a dilute collection of noninteracting damped harmonic oscillators.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. A method for testing alkali halide crystals with anisotropic centers for performance as holographic storage media and for optimum operating parameters which comprises:

passing linearly polarized light of known wavelength through an alkali halide crystal with aligned anisotropic centers so that polarization of said light is linearly polarized at 45° with respect to the alignment direction of said anisotropic centers;

analyzing said light upon exit from said crystal now ellipically polarized in order to determine the maximum and minimum intensities, the angle between the minimum intensity and the direction perpendicular to the alignment axis, and the intensities of said exited light with polarization parallel and perpendicular to the alignment of said anisotropic centers, and the optical density of said crystal for light linearly polarized parallel and perpendicular to the optical axis of said aligned anisotropic centers;

repeating said analysis of said light for different wavelengths of said light; and calculating the maximum diffraction efficiency for each of said analyses.

2. The method of claim 1 wherein the maximum diffraction efficiency is calculated by calculating the phase difference from the equation:

$$\delta = \cos^{-1}\left[\frac{1+\left(\frac{a_{11}}{a_\perp}\tan\theta\right)^2 - \left[\tan\theta + \left(\frac{a_{11}}{a_\perp}\right)^2\right]\frac{I_L}{I_M}}{2\sqrt{\frac{I_{11}}{I}}\tan\theta\left[1+\frac{I_L}{I_M}\right]}\right]$$

and by calculating the value of the diffraction efficiency equation:

$$\eta = \left[\sin^2\frac{\delta}{4\cos\theta} + \sinh^2\frac{D_o}{4(0.8686)\cos\theta_o}\right]\exp\left(-\frac{D_o'}{(0.8686)\cos\theta_o}\right).$$

3. The method of claim 1 wherein said alkali halide is NaF and said anisotropic center is M-center.

4. The method of claim 1 wherein said alkali halide is NaF and said anisotropic center is $M_A$ center.

5. The method of claim 1 wherein said alkali halide is KCl and said anisotropic center is M-center.

* * * * *